(12) United States Patent
Tian

(10) Patent No.: US 9,005,595 B2
(45) Date of Patent: Apr. 14, 2015

(54) CHINESE MEDICINE HAIR-BLACKENING PREPARATION AND FORMULA AND PREPARATION METHOD THEREFOR

(75) Inventor: Zhiyuan Tian, Guangdong (CN)

(73) Assignee: Zhixian Yuan, Guangdong (CN)

( * ) Notice: Subject to any disclaimer, the term of this patent is extended or adjusted under 35 U.S.C. 154(b) by 54 days.

(21) Appl. No.: 13/811,667

(22) PCT Filed: Oct. 26, 2011

(86) PCT No.: PCT/CN2011/081325
§ 371 (c)(1),
(2), (4) Date: Jan. 23, 2013

(87) PCT Pub. No.: WO2012/059012
PCT Pub. Date: May 10, 2012

(65) Prior Publication Data
US 2013/0121941 A1    May 16, 2013

(30) Foreign Application Priority Data

Nov. 1, 2010 (CN) .......................... 2010 1 0532864

(51) Int. Cl.

| | | |
|---|---|---|
| *A61K 8/98* | (2006.01) | |
| *A61K 8/34* | (2006.01) | |
| *A61K 8/92* | (2006.01) | |
| *A61K 8/97* | (2006.01) | |
| *A61Q 5/06* | (2006.01) | |
| *A61Q 5/00* | (2006.01) | |
| *A61K 36/815* | (2006.01) | |
| *A61K 36/889* | (2006.01) | |
| *A61K 36/9068* | (2006.01) | |
| *A61K 36/185* | (2006.01) | |
| *A61K 36/232* | (2006.01) | |
| *A61K 36/236* | (2006.01) | |
| *A61K 36/287* | (2006.01) | |
| *A61K 36/48* | (2006.01) | |
| *A61K 36/481* | (2006.01) | |
| *A61K 36/537* | (2006.01) | |
| *A61K 36/605* | (2006.01) | |
| *A61K 36/704* | (2006.01) | |

(52) U.S. Cl.
CPC . *A61K 8/981* (2013.01); *A61K 8/34* (2013.01); *A61K 8/925* (2013.01); *A61K 8/97* (2013.01); *A61Q 5/06* (2013.01); *A61Q 5/00* (2013.01); *A61K 35/57* (2013.01); *A61K 36/815* (2013.01); *A61K 36/889* (2013.01); *A61K 36/9068* (2013.01); *A61K 36/185* (2013.01); *A61K 36/232* (2013.01); *A61K 36/236* (2013.01); *A61K 36/287* (2013.01); *A61K 36/48* (2013.01); *A61K 36/481* (2013.01); *A61K 36/537* (2013.01); *A61K 36/605* (2013.01); *A61K 36/704* (2013.01)

(58) Field of Classification Search
CPC .......... A61K 8/891; A61K 8/981; A61K 8/34
USPC ....................................... 424/70.6
See application file for complete search history.

(56) References Cited

PUBLICATIONS

Louise M., downloaded from http://unitproj.library.ucla.edu/biomed/spice/index.cmf) on May 2, 2014.*
Legume web, downloaded from http://www.ildis.org/LegumeWeb?version~10.01&LegumeWeb&tno~16104&genus~Astragalus&species~propinquus on May 2, 2014.*
Ram et al., downloaded from http://www.hort.purdue.edu/newcrop/proceedings1990/v1-225.html on May 2, 2014.*
Roach J., downloaded from http://news.nationalgeographic.com/news/pf/15119340.html on May 2, 2014.*
Schmid, Title: Cancer resar yields clues to why hair turns gray; published by Accosiated press, Dec. 23, 2014.*
Definition of melocytes from Encyclopedia Britannica.*
Kreeger; Title: First Study to Convert Adult Human Cells to Hair-Follicle-Generating Stem Cells has Implications for Hair Regeneration; Penn Mediciane News, published online Jan. 28, 2014.*

* cited by examiner

*Primary Examiner* — Ali Soroush
*Assistant Examiner* — Yanzhi Zhang

(57) ABSTRACT

A Chinese medicine hair-blackening preparation and formula and a preparation method therefor, wherein the preparation comprises ginger, *astragalus mongholicus, polygonum multiflorum*, black sesame, *angelica sinensis, fructus lycii, ligusticum wallichii, salvia miltiorrhizae, chrysanthemum indicum*, red dates, black soya bean, walnuts, cortex mori radicis, fructus liqustri lucidi, eclipta alba, mulberry fruit, fat extract of silkie, fat extract of duck, 65% ethanol solution and 40% ethanol solution; the preparation is prepared by using techniques of mixing, grinding, soaking and extraction to produce an ointment; the preparation is suitable for all hair and scalp types, and when it is used after hair wash, it produces no allergic reactions or toxic side-effects, thereby allowing the medically active elements to penetrate quickly into the skin and to be absorbed by the skin to achieve quickly visible hair blackening effect.

3 Claims, No Drawings

CHINESE MEDICINE HAIR-BLACKENING PREPARATION AND FORMULA AND PREPARATION METHOD THEREFOR

BACKGROUND OF THE INVENTION

The invention refers to a Chinese material medica composition beneficial for the growth of black hair, and to be specific, the invention is related to a Chinese material medica composition and its preparation method beneficial for the growth of black hair.

With a high efficient and fast-paced way of life in modern city, more and more people begin to be worried about the growth of white hair. Worse still, this phenomenon even become increasingly serious especially among young people for they usually have to be concerned about that their black hair will be turned into white hair at an early stage. Currently, though there are many pharmaceutical preparations for treating white hair in the market, firstly the western medicine is relatively expensive for the patients have to continuously receive several courses of treatment, which will increase a heavy economic burden for the patients and secondly, the bodies of patients will suffer from a certain side effect due to the long time use of such medication. As to the pure traditional Chinese medicine in the market it has a slow efficacy and instability. Thus although it temporarily enables part of white hair to turn black due to the stimulation of hair follicle of head, the white hair will appear again and the black hair will even shed once stop using medication. The main reason is that the pathological changes of hair follicle are related to the lack of nutrition of hair growth environment. Therefore, patients need a medication with a good efficacy which enables white hair to continuously turn black and a relatively inexpensive price to tackle the mentioned problem.

BRIEF SUMMARY OF THE INVENTION

The invention is aimed to offer a composition of Chinese materia medica beneficial for the growth of black hair and to be specific to offer a composition of Chinese materia materia and its method of preparation beneficial for the growth of black hair by combining modern Chinese and western medicine technology, on the basis of the secret prescription handed down from the ancestors and according to the deficiencies of the above present technology. The preparation made by the invention can be applied to various hair scalps without any anaphylaxis and non-toxic side effect after using it to clean hair, which enables medicine to penetrate into skin quickly and achieve the goal of promoting the growth of black hair with a quick and good effect, low cost and a simple and feasible preparation process.

The technical plan of the invention is as follows:

The invention is a thick paste composition which is prepared by mixing ginger, *astragalus mongholicus, polygonum multiflorum*, black sesame, *angelica sinensis, fructus lycii, ligusticum wallichii, salviae miltiorrhizae, chrysanthemum indicum*, red dates, black soya bean, walnuts, cortex mori radicis, fructus ligustri lucidi, eclipta alba, mulberry, fat extract of silkie and duck, in addition, 65% ethanol solution and 40% ethanol solution.

Wherein the quality of each composition is:
Ginger 55-100 g
*Astragalus mongholicus* 75-100 g
*Polygonum multiflorum* 100-150 g
Black sesame 80-90 g
*Angelica sinensis* 60-120 g
*Fructus lycii* 85-125 g
*Ligusticum wallichii* 60-80 g
*Salviae miltiorrhizae* 75-95 g
*Chrysanthemum indicum* 40-50 g
Red dates 60-100 g
Black soya bean 100-120 g
Walnuts 50-80 g
Cortex mori radicis 62-80 g
Fructus ligustri lucidi 30-40 g
Eclipta alba 40-80 g
Mulberry 60-80 g
A silkie,
A duck.
In addition,
65% Ethanol solution 2000-3000 g 40% Ethanol solution 2800-3500 g.

In order to obtain a better effect, the amount of raw material of the invention can be optimized as follows:
Ginger 60-80 g
*Astragalus mongholicus* 80-90 g
*Polygonum multiflorum* 100-120 g
Black sesame 80-90 g
*Angelica sinensis* 60-100 g
*Fructus lycii* 90-100 g
*Ligusticum wallichii* 70-80 g
*Salviae miltiorrhizae* 80-90 g
*Chrysanthemum indicum* 40-50 g
Red dates 80-100 g
Black soya bean 100-120 g
Walnuts 70-80 g
Cortex mori radicis 70-80 g
Fructus ligustri lucidi 30-40 g
Eclipta alba 40-60 g
Mulberry 60-80 g
A silkie,
A duck.
In addition,
65% Ethanol solution 2000-2500 g 40% Ethanol solution 2800-3000 g.

Of course, in order to obtain further better effect, the quality of the raw material of the invention can still be optimized as follows:
Ginger 80 g
*Astragalus mongholicus* 90 g
*Polygonum multiflorum* 100 g
Black sesame 90 g
*Angelica sinensis* 100 g
*Fructus lycii* 90 g
*Ligusticum wallichii* 80 g
*Salviae miltiorrhizae* 85 g
*Chrysanthemum indicum* 45 g
Red dates 85
Black soya bean 105 g
Walnuts 75 g
Cortex mori radicis 80 g
Fructus ligustri lucidi 40 g
Eclipta alba 60 g
Mulberry 80 g
A silkie,
A duck.
In addition,
65% Ethanol solution 2000 g 40% Ethanol solution 2800 g.

The mentioned method of preparation of Chinese material medica beneficial for the growth of black hair includes the following steps:

1). Prepare the Chinese materia medica formula mixed with ginger, *astragalus mongholicus, polygonum multiflorum*, black sesame, *angelica sinensis, fructus lycii, ligusticum*

*wallichii, salviae miltiorrhizae* and *chrysanthemum indicum* in proportion and put it at a high temperature of 50-70° C. for drying and then naturally cool it down to room temperature;

2). Put the above Chinese materia medica formula into the grinder for grinding and then reserve as powder after a 80 mesh sieve;

3). Prepare the Chinese material medica formula mixed with red dates, black soya bean, walnuts, cortex mori radicis, fructus ligustri lucidi, eclipta alba and mulberry in proportion and put it at a high temperature of 70-80° C. for drying and then naturally cool it down to room temperature;

4). Put the above Chinese material medica formula into the grinder for grinding and then reserve as powder after a 80 mesh sieve;

5). Take out 200 g of internal fats of each silkie and duck after their slaughters and put them into a clean bowl and then add 20 ml water into the bowl so as to put them into the pot for 10 minutes' steaming and reserve fresh oil after filtration.

6). Put the composition obtained from the second step into 40% ethanol solution which is equivalent to 2 times of quality of the original amount for 3-5 days' soakage and then release the soakage solution for reservation;

7). Then put the above soaked residue of composition into 65% ethanol solution that is equivalent to 1.5 times of the original amount for 3 days' soakage and release the soakage solution for use;

8). Combine and filtrate the above two soakage solutions and concentrate the solutions into a thick paste with a proportion of 0.28-1.3 for use after retrieving ethanol solution;

9). Put the composition prepared by the fourth step into the 40% ethanol solution that is equivalent to 2 times of quality of the original amount for 5 days' soakage and then release and filtrate the soakage solution for use;

10). Then put the above soaked residue of composition into 40% ethanol solution that is equivalent to 1.5 times of the original amount for 5 days' soakage, then release and filtrate the soakage solution for use;

11). Combine and filtrate the above two soakage solutions and concentrate the solutions into a thick paste with a proportion of 0.28-1.3 for use after retrieving ethanol solution;

12). Mix the thick paste compositions prepared by the eighth and eleventh steps, add the fresh fat oil of silkie and duck obtained from the fifth step, then stir evenly, package and sterilize the above mixture and such a Chinese materia medica preparation can be obtained.

When you use the above preparation you can take a proper amount of it and put it on your head. After that, please wipe and massage your scalp as well as wash your hair with clean water. If you use it for a long-time you will receive a good effect, which will enable your white hair to turn black gradually and maintain medical efficacy.

Generally speaking, the hairs of young people are black and shinny while the hairs of old people are often white and grey. The reason for why people will have black hair is that there is a melanin in their hairs and the more melanin hair contains, blacker hair will become; on the contrary, the less melanin hair contains, lighter the color of hair will become. With the aging of human body, the pigment cells in the hair follicle will stop producing melanin thus black hair will also begin to turn white. However, there is no uniform gland that secretes melanin in human body and melanin will be generated in each strand of hair respectively therefore hair will always turn white one by one. Although the causes of the generation of white hair has not been fully understood so far, from clinical points of view the common predisposing factors mainly include: chronic disease, endocrine dyscrasia, denutrition and familial inheritance. If the melanin generated in the hairs of young people fails to be carried to the root of hair, it will be reduced thus black hair will begin to turn white day by day. According to the above theory, the invention nourishes and stimulates the hair follicle of the root of hair, which enables melanin to be carried to all parts of hair smoothly.

There are various Chinese material medica related to hair growth and hair breeding in the herbal documents of ancient China, among which many of them have been verified with a good efficacy by modern medicine. No matter people in the foreign countries or those in China pay highly attention to the hair growth and hair breeding of Chinese material medica. In the invention, Silkie is mild in property and sweet in taste without toxicity and can penetrate into liver and kidney meridians. With rich vitamin, trace element, protein and 18 amino acids it has the efficacy of nourishing Yin and removing heat, nourishing liver and kidney and nourishing Qi and blood, which can promote hair growth and is beneficial for the nourishment of scalp and protection of hair.

*Astragalus mongholicus* contains various amino acid, betaine, folic acid, alkaloid and trace element needed for human body and it is conducive to expand blood vessels, improve nutrition of skin and prevent the generation of yellow hair and white hair.

*Polygonum multiflorum* contains nutritious ingredients of lecithin and has the efficacy of nourishing blood and expelling wetness, regulating nervus and incretion, providing nutrition for hair root, enhancing the generation of hair melanin and making hair become blacker. At the same time, it still contains chrysophanol and a great deal of starch. The glucose generated by the hydrolysis of starch can provide nourishment for hair and is also the best raw material of Chinese material medica used for the preparation of hair conditioning agent. According to the experimental demonstration of modern pharmacology, lecithin contained in *polygonum multiforum* is an important raw material of cell membrane, which can promote the metabolism and growth and development of cells, delay senium of cells and prolong life.

Black sesame contains glyceride, lecithin, calcium, phosphorus and ferrum. Wherein the content of ferrum in black ant ranks in the front of various other medicines and it is able to enrich blood, moisten the skin and nourish hair. In addition, it is an ideal roborant for the nourishment of liver and kidney and the five internal organs and can be used to treat the symptom of early white hair and anemia of hair as well as yellow hair. Moreover, it is beneficial to treat lipsotrichia and promote the growth of hair and has become one of the commonly used medicines among the formula of cosmetology and hairdressing.

*Angelica sinensis* can promote the circulation of blood, enrich blood and relieve pain and moisten skin. In addition, it is still able to expand blood capillary of scalp and skin, promote the circulation of blood and prevent the shortage of vitamin E. *Angelica sinensis* shampoo made from *angelica sinensis* extract can prevent lipsotrichia, moisten skin and hair and bring you a shinny black hair as well as prevent hair becoming yellow and white.

*Fructus lycii* contains vitamin A1, B2 and C necessary to cosmetology and trace elements such as calcium, phosphorus and ferrumm, among which the contents of vitamin A and C are the highest. If extract of *alternanthera sessilis* is added into cosmetics, it can prevent lipsotrichia, bring you a shinny and black hair and has a notable efficacy on treating yellow and white hair, pale complexion and dry skin caused by the lack of vitamin and trace element necessary to the body. Due to the fact that it can still promote the generation of melanin of hair thus it has a good efficacy on the treatment of alopecia areata.

*Ligusticum wallichii* has a good effect on dispelling wind, invigorating the circulation of blood, moistening skin and relieving itching, which is beneficial for the improvement of facial nutrition. It has been testified by modern pharmacology that *ligusticum wallichii* can expand blood capillary of head, boost blood circulation, increase nutrition of hair and make hair become more flexible and hardened. Moreover, it is still able to delay the growth of white hair and maintain the smooth and luster of hair.

*Salviae miltiorrhizae* is a labiate plant which is slightly cold in property and bitter in taste. Its chemical constituent includes tanshinone I, IIA and IIB, isotanshinone I and IIA, cryptotanshinone, isocryptotanshinone, methylation of tanshinone and hydroxyl of tanshinone. The main efficacy of *salviae miltiorrhizae* is to invigorate the circulation of blood and remove stasis. Since it contains rich vitamin and trace element of zinc, cooper and ferrum, it can promote the generation of melanin of hair and improve the symptom of white and yellow hair and dried hair caused by the lack of trace element. Meanwhile, because *salviae miltiorrhizae* itself is red thus its red alkannin will be dissolved into oil after stewed. Thus it can be used for makeup and cosmetics and added into various maquillages or applied to other natural medicines, which has a variety of functions such as relieving itching, getting rid of dandruff, preventing and treating lipsotrichia, promoting hair growth, moistening hair and enhance the elasticity of skin.

*Polygonum multiflorum* is a root tuber of polygonaceae polygonum plants with a mild property and a bitter and puckery taste. Its chemical constituent contains lecithin emodin, chryso-phanol, rhein and physcion etc. Lecithin can be found in the root tuber of *polygonum multiflorum* and it is a main ingredient of nervous tissue, especially myelencephalon and meanwhile is an important raw material of blood cell and other cell membranes. It can promote the rebirth and development of blood cells. The people with lipsotrichia and white hair usually fail to provide adequate blood and nourishment for their hair. *Polygonum multiflorum* can nourish the blood of liver and kidney and can receive a better effect on treating white hair and lipsotrichia, especially for seborrheic lipsotrichia.

At the same time, ethanol solution can be used as surface active agent strengthening recuperation and combining with calcium and magnesium ion in the water to further enhance the elasticity and luster of hair and make hair become loose and easily to be combed.

Clinical Experiment 1:

1). Time of observation: Under the circumstances that the technical plan of the invention has not been disclosed, the six month from February of 2009 to July of 2009 are chosen as the time of observation.

2). Object of observation: Select 40 patients for the case of illness: 20 male patients and 20 female patients; age: 18 cases for 16 to 25 years old and 22 cases for 25 to 35 years old; occupation: 10 cases of students and 10 cases of workers, 5 cases of farmers, 10 cases of teachers and 5 cases for others. Course of disease: from the time of paroxysm to time of treatment, 20 cases within 2 years, 10 cases from 2 years to 4 years and 10 cases of more than 4 years.

3). Method of use: use the shampoo made from the preparation of the invention to wash hair 3 times a day and the above procedure should be done after 1 hour's dinner each time; 1 month is equivalent to 1 course of treatment thus 6 courses of treatment are regarded as the observation of treatment efficacy.

4). Observation of effect:

The standard of effect is divided into: remarkableness, which means that the percentage of white hair turning into black hair is more than 85%; effectiveness, which means that the percentage of white hair turning into black hair is more than 50% and the symptom of white hair can be controlled; invalidity, which means that the symptom of white hair has not been improved or alleviated basically.

Out of 40 cases of the results, there are 20 cases of remarkableness, 13 cases of effectiveness and 7 cases of invalidity and the total effective rate is 82.5%.

Clinical Experiment 2:

1). Time of observation: Under the circumstances that the technical plan of the invention has not been disclosed, the six month from January of 2008 to June of 2008 are chosen as the time of observation.

2). Object of observation: Select 20 cases of illnesses: 10 cases for male and 10 cases for female; age: 8 cases for 16 to 25 years old and 12 cases for 25 to 35 years old; occupation: 10 cases of students and 2 cases of workers, 2 cases of farmers, 2 cases of teachers and 4 cases for others. Course of disease: from the time of paroxysm to time of treatment, 10 cases within 2 years, 5 cases from 2 years to 4 years and 5 cases of more than 4 years.

3). Method of use: use the shampoo made from the preparation of the invention to wash hair 3 times a day and the above procedure should be done 1 hour before meal time each time; 1 month is equivalent to 1 course of treatment thus 6 courses of treatment are regarded as the observation of treatment efficacy.

4). Observation of effect:

The standard of effect is divided into: remarkableness, which means that the percentage of white hair turning into black hair is more than 85%; effectiveness, which means that the percentage of white hair turning into black hair is more than 50% and the symptom of white hair can be controlled; invalidity, which means that the symptom of white hair has not been improved or alleviated basically.

Out of 20 cases of the results, there are 14 cases of remarkableness, 2 cases of effectiveness and 4 cases of invalidity and the total effective rate is 80%.

Through combining the above clinical data and the theoretical evidence of the invention, the beneficial effect of the invention lies in: the preparation of the invention can be applied to various hair and scalps without any anaphylaxis and non-toxic side effect after using it to clean hair, which enables medicine to penetrate into skin quickly and achieve the goal of growth of black hair with a quick and good effect, low cost and a simple and feasible preparation process.

DETAILED DESCRIPTION OF THE INVENTION

The invention will be given further detailed explanation by combining the following implementation examples:

Implementation Example 1

The quality of raw material of the invention can be optimized as follows (g):

Ginger 100 g
*Astragalus mongholicus* 100 g
*Polygonum multiflorum* 150 g
Black sesame 80 g
*Angelica sinensis* 60 g

*Fructus lycii* 85 g
*Ligusticum wallichii* 60 g
*Salviae miltiorrhizae* 95 g
*Chrysanthemum indicum* 50 g
Red dates 60 g
Black soya bean 120 g
Walnuts 80 g
Cortex mori radicis 80 g
Fructus ligustri lucidi 40 g
Eclipta alba 40 g
Mulberry 60 g,
A silkie,
A duck.
In addition,
65% Ethanol solution 2000 g 40% Ethanol solution 3000 g.

The mentioned method of preparation of promoting the growth of black hair and hair breeding includes the following steps:

1). Prepare the Chinese materia medica formula mixed with ginger, *astragalus mongholicus, polygonum multiflorum*, black sesame, *angelica sinensis, fructus lycii, ligusticum wallichii, salviae miltiorrhizae* and *chrysanthemum indicum* in proportion and put it at a high temperature of 50-70° C. for drying and then naturally cool it down to room temperature;

2). Put the above Chinese materia medica formula into the grinder for grinding and then reserve as powder after a 80 mesh sieve;

3). Prepare the Chinese material medica formula mixed with red dates, black soya bean, walnuts, cortex mori radicis, fructus ligustri lucidi, eclipta alba and mulberry in proportion and put it at a high temperature of 70-80° C. for drying and then naturally cool it down to room temperature;

4). Put the above Chinese material medica formula into the grinder for grinding and then reserve as powder after a 80 mesh sieve;

5). Take out 200 g of internal fats of each silkie and duck after their slaughters and put them into a clean bowl and then add 20 ml water into the bowl so as to put them into the pot for 10 minutes' steaming and reserve fresh oil after filtration.

6). Put the composition obtained from the second step into 40% ethanol solution which is equivalent to 2 times of quality of the original amount for 3-5 days' soakage and then release the soakage solution for reservation;

7). Then put the above soaked residue of composition into 65% ethanol solution that is equivalent to 1.5 times of the original amount for 3 days' soakage and release the soakage solution for use;

8). Combine and filtrate the above two soakage solutions and concentrate the solutions into a thick paste with a proportion of 1.28-1.3 for use after retrieving ethanol solution;

9). Put the composition prepared by the fourth step into the 40% ethanol solution that is equivalent to 2 times of quality of the original amount for 5 days' soakage and then release and filtrate the soakage solution for use;

10). Then put the above soaked residue of composition into 40% ethanol solution that is equivalent to 1.5 times of the original amount for 5 days' soakage, then release and filtrate the soakage solution for use;

11). Combine and filtrate the above two soakage solutions and concentrate the solutions into a thick paste with a proportion of 1.28-1.3 for use after retrieving ethanol solution;

12). Mix the thick paste compositions prepared by the eighth and eleventh steps, add the fresh fat oil of silkie and duck obtained from the fifth step, then stir evenly, package and sterilize the above mixture and such a Chinese materia medica preparation can be obtained.

Implementation Example 2

The quality of raw material of the invention can still be optimized as follows (g):
Ginger 65 g
*Astragalus mongholicus* 85 g
*Polygonum multiflorum* 110 g
Black sesame 90 g
*Angelica sinensis* 65 g
*Fructus lycii* 95 g
*Ligusticum wallichii* 75 g
*Salviae miltiorrhizae* 85 g
*Chrysanthemum indicum* 50 g
Red dates 85 g
Black soya bean 105 g
Walnuts 75 g
Cortex mori radicis 80 g
Fructus ligustri lucidi 34 g
Eclipta alba 45 g
Mulberry 70 g,
A silkie,
A duck.
In addition,
65% Ethanol solution 2000 g 40% Ethanol solution 2800 g.

The method of preparation is the same as implementation 1.

Implementation Example 3

Wherein the quality of each composition is (g):
Ginger 80 g
*Astragalus mongholicus* 90 g
*Polygonum multiflorum* 100 g
Black sesame 90 g
*Angelica sinensis* 100 g
*Fructus lycii* 90 g
*Ligusticum wallichii* 80 g
*Salviae miltiorrhizae* 85 g
*Chrysanthemum indicum* 45 g
Red dates 85 g
Black soya bean 105 g
Walnuts 75 g
Cortex mori radicis 80 g
Fructus ligustri lucidi 40 g
Eclipta alba 60 g
Mulberry 80 g
A silkie,
A duck.
In addition,
65% Ethanol solution 2000 g 40% Ethanol solution 2800 g.

The method of preparation is the same as implementation 1.

Implementation Example 4

Wherein the quality of each composition is (g):
Ginger 80 g
*Astragalus mongholicus* 93 g
*Polygonum multiflorum* 115 g
Black sesame 88 g
*Angelica sinensis* 68 g
*Fructus lycii* 88 g
*Ligusticum wallichii* 78 g
*Salviae miltiorrhizae* 78 g

*Chrysanthemum indicum* 48 g
Red dates 60 g
Black soya bean 105 g
Walnuts 58 g
Cortex mori radicis 68 g
Fructus ligustri lucidi 38 g
Eclipta alba 48 g
Mulberry 68 g,
A silkie,
A duck.
In addition,
65% Ethanol solution 2000 g 40% Ethanol solution 2800 g.
The method of preparation is the same as implementation 1.

The mentioned implementation examples are only several examples among the numerous modes of implementation of the invention. If the dose has been increased or reduced according to the proportion of technical plans in each formula, the treatment efficacy will not be influenced by the preparation and it should also be included within the right protection scope of the invention.

What is claimed is:

1. A method of preparing a Chinese materia medias preparation beneficial for darkening white hair, wherein the method comprises the following steps:

step 1: mixing 55-100 g of ginger, 75-100 g of *astragalus mongholicus*, 100-150 g of *polygonum multiflorum*, 80-90 g of black sesame, 60-120 g of *angelica sinensis*, 85-125 g of *fructus lycii*, 60-80 g of *ligusticum wallichii*, 75-95 g of *salviae miltiorrhizae* and 40-50 g of *chrysanthemum indicum* to form a first mixture, putting the first mixture at a temperature of 50-70° C. for drying, and then cooling the first mixture to room temperature;

step 2: putting the first mixture obtained in step 1 into a grinder, grinding the first mixture to a powder, then sieving the powder through an 80 mesh sieve and saving the obtained powder for later use;

step 3: mixing 60-100 g of red dates, 100-120 g of black soya bean, 50-80 g of walnuts, 62-80 g of *cortex mori radicis*, 30-40 g of *fructus ligustri lucidi*, 40-80 g of eclipta alba and 60-80 g of mulberry fruit to form a second mixture, putting the second mixture at a temperature of 70-80° C. for drying, and then cooling the second mixture to room temperature;

step 4: putting the second mixture obtained in step 3 into a grinder, grinding the second mixture to a powder, then sieving the powder through an 80 mesh sieve and saving the obtained powder for later use;

step 5: taking 200 g of internal fat from a silkie and 200 g of internal fat from a duck, placing the fats into a clean bowl, then adding 20 ml of water into the bowl; steaming the bowl over a pot for 10 minutes to obtain oil, filtering the oil, and reserving the filtered oil for later use;

step 6: putting the powder obtained in step 2 into a 40% ethanol solution which has a mass 2 times a mass of the powder obtained in step 2, soaking the powder obtained in step 2 in the 40% ethanol solution for 3-5 days; and then pouring out a first soakage solution for later use;

step 7: putting the powder after soakage as obtained in step 6 into 2000-3000 g of 65% ethanol solution that has a mass 1.5 times a mass of the powder after soakage as obtained in step 6, soaking the powder after soakage as obtained in step 6 in the 65% ethanol solution for 3 days; and then pouring out a second soakage solution for later use;

step 8: combining the first soakage solution obtained in step 6 and the second soakage solution obtained in step 7, filtering the combined first and second soakage solutions, retrieving the 40% ethanol solution used in step 6 and the 65% ethanol solution used in step 7 from the combined and filtered first and second soakage solutions, and then concentrating the combined and filtered first and second soakage solutions into a paste having a concentration density of 1.28-1.3 for later use;

step 9: putting the powder obtained in step 4 into a 40% ethanol solution that has a mass 2 times a mass of the powder obtained in step 4, soaking the powder obtained in step 4 into the 40% ethanol solution of step 9 for 5 days; pouring out a third soakage solution and then filtering the third soakage solution for later use;

step 10: putting the powder after soakage as obtained in step 9 into a 40% ethanol solution that has a mass 1.5 times a mass of the powder after soakage as obtained in step 9, soaking the powder after soakage as obtained in step 9 in the 40% ethanol solution of step 10 for 5 days, releasing a fourth soakage solution and then filtering the fourth soakage solution for later use;

step 11: combining the third and fourth soakage solutions obtained respectively in step 9 and step 10, filtering the combined third and fourth soakage solutions, retrieving the 40% ethanol solutions used in steps 9 and 10 from the combined and filtered third and fourth soakage solutions, and then concentrating the combined and filtered third and fourth soakage solutions into a paste having a concentration density of 1.28-1.3 for later use;

step 12: mixing the pastes prepared in step 8 and step 11, adding the filtered oil obtained in step 5 into the mixed pastes, stirring the mixed pastes evenly to obtain a final mixture, finally, packing and sterilizing the final mixture to obtain the Chinese materia medica preparation; and wherein a total amount of the 40% ethanol solution used in steps 6, 9 and 10 is 2800-3500 g.

2. The method of preparing a Chinese materia *medica* preparation beneficial for darkening white hair as in claim 1, wherein the method comprises:

using 60-80 g of the ginger in step 1;
using 80-90 g of the *astragalus mongholicus* in step 1;
using 100-120 g of the *polygonum multiflorum* in step 1;
using 60-100 g of the *angelica sinensis* in step 1;
using 90-100 g of the *fructus lycii* in step 1;
using 70-80 g of the *ligusticum wallichii* in step 1;
using 80-90 g of the *salviae miltiorrhizae* in step 1;
using 80-100 g of the red dates in step 3;
using 70-80 g of the walnuts in step 3;
using 70-80 g of the cortex mori radicis in step 3;
using 30-40 g of the fructus ligustri lucidi in step 3;
using 40-60 g of the *eclipta alba* in step 3;
using 2000-2500 g of the 65% ethanol solution in step 7; and
using a total amount of 2800-3000 g of the 40% ethanol solution in steps 6, 9 and 10.

3. The method of preparing a Chinese materia medics preparation beneficial for darkening white hair as in claim 1, wherein the method comprises:

using 80 g of the ginger in step 1;
using 90 g of the *astragalus mongholicus* in step 1;
using 100 g of the *polygonum multiflorum* in step 1;
using 90 g of the black sesame in step 1;
using 100 g of the *angelica sinensis* in step 1;
using 90 g of the *fructus lycii* in step 1;

using 80 g of the *ligusticum wallichii* in step 1;
using 85 g of the *salviae miltiorrhizae* in step 1;
using 45 g of the *chrysanthemum indicum* in step 1;
using 85 g of the red dates in step 3;
using 105 g of the black soya bean in step 3;
using 75 g of the walnuts in step 3;
using 80 g of the cortex mori radicis in step 3;
using 40 g of the fructus ligustri lucidi in step 3;
using 60 g of the eclipta alba In step 3;
using 80 g of the mulberry fruit in step 3;
using 2000 g of the 65% ethanol solution in step 7; and
using a total amount of 2800 g of the 40% ethanol solution in steps 6, 9 and 10.

\* \* \* \* \*